United States Patent

Rohringer et al.

[11] Patent Number: 6,143,888
[45] Date of Patent: Nov. 7, 2000

[54] USE OF TRIAZINE-BASED UVAS FOR USE AS QUENCHERS IN PAPER-MAKING PROCESSES

[75] Inventors: Peter Rohringer, Schönenbuch, Switzerland; Dieter Reinehr, Kandern; Robert Hochberg, Freiburg, both of Germany; Georges Metzger, Moernach, France

[73] Assignee: Ciba Specialty Chemicals Corporation, Tarrytown, N.Y.

[21] Appl. No.: 09/194,767

[22] PCT Filed: May 22, 1997

[86] PCT No.: PCT/EP97/02606

§ 371 Date: Dec. 2, 1998

§ 102(e) Date: Dec. 2, 1998

[87] PCT Pub. No.: WO97/46541

PCT Pub. Date: Dec. 11, 1997

[30] Foreign Application Priority Data

Jun. 4, 1996 [GB] United Kingdom .................... 9611614

[51] Int. Cl.$^7$ ........................... C07D 251/68; C09K 11/06
[52] U.S. Cl. .................. 544/193.2; 252/301.23; 252/600; 427/158; 544/206
[58] Field of Search ................. 544/193.2, 206; 252/301.23, 600; 427/158

[56] References Cited

U.S. PATENT DOCUMENTS

| | | |
|---|---|---|
| 3,118,887 | 1/1964 | Hardy et al. ............................. 260/248 |
| 3,351,557 | 11/1967 | Almstead et al. ....................... 252/106 |
| 3,725,074 | 4/1973 | Shiba et al. ............................... 96/122 |
| 3,995,997 | 12/1976 | Boehmke et al. ............................ 8/84 |
| 4,098,954 | 7/1978 | Raspanti ................................. 428/537 |
| 4,252,604 | 2/1981 | Fleck et al. .......................... 544/193.2 |
| 4,695,405 | 9/1987 | Harnisch et al. ....................... 252/600 |
| 4,950,304 | 8/1990 | Reinert et al. ............................. 8/566 |
| 5,197,991 | 3/1993 | Rembold ................................... 8/490 |

FOREIGN PATENT DOCUMENTS

| | | |
|---|---|---|
| 2113443 | 9/1971 | Germany . |
| 2341293 | 3/1975 | Germany . |
| 4401471 | 7/1994 | Germany . |
| 1033388 | 10/1963 | United Kingdom . |
| 1114861 | 4/1965 | United Kingdom . |
| 2298422 | 9/1996 | United Kingdom . |

OTHER PUBLICATIONS

Chem. Abstr. 114:83877n (1991).

Chem. Abstr. 113:14657h (1990).

Chem. Abstr. 118:112904j (1993).

*Primary Examiner*—Mukund J. Shah
*Assistant Examiner*—Venkataraman Balasubramanian
*Attorney, Agent, or Firm*—Kevin T. Mansfield

[57] ABSTRACT

The present invention provides a process for the inhibition (quenching) of the effect of an anionic fluorescent whitening agents on a substrate, comprising treating the substrate with a triazine UVA compound, some of which are new compounds.

13 Claims, No Drawings

USE OF TRIAZINE-BASED UVAS FOR USE AS QUENCHERS IN PAPER-MAKING PROCESSES

The present invention relates to a process for inhibiting (quenching) the effect of anionic fluorescent whitening agents on substrates, especially on fibre materials, by treating the substrates with certain triazine-based ultra-violet absorption agents (UVAs), some of which are new compounds.

The fluorescent whitening effect exerted by fluorescent whitening agents on fibre materials treated with the said by fluorescent whitening agents, provides a valuable and aesthetically appealing whiteness improvement in the appearance of fibre materials so treated.

Particularly in the paper industry, however, there are situations in which the fluorescent whitening effect exerted by fluorescent whitening agents can lead to problems. For example, many paper-producing machines are required to produce, alternately, whitened and non-whitened paper. Problems arise when, after the machine has been used to produce whitened paper, it is subsequently-required for the production of non-whitened paper. In these circumstances, residual fluorescent whitening agent from the production of whitened paper remains on the machine parts and contaminates the paper obtained in the subsequent production of non-whitened paper.

It is possible, of course, to thoroughly clean the paper machine and its associated recycling systems whenever it has been used to produce whitened paper and is then immediately to be used to produce non-whitened paper. Such thorough ceaning is expensive, however, and impairs production capacity.

It has already been proposed, in DE-A-2 448 293, to apply a quencher compound to paper material which is not be whitened before or after sheet formation. Such quencher compounds have also been suggested for addition to whitened used paper from which non-whitened paper is to be produced.

The quencher compounds used in DE-A-2 448 293 are water-soluble acid addition salts or quaternary ammonium salts of compounds which contain a group of formula:

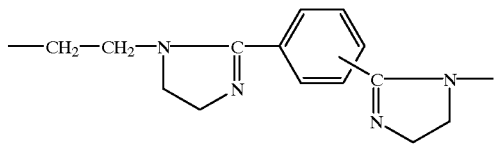

in which the substituents on the phenyl nucleus are in m- or p-position to one another.

Most modern paper-making processes, however, are operated under neutral pH conditions and the compounds of DE-A-2 448 293 are unsatisfactory for such use since they only partly absorb on to the fibre under neutral application conditions. As a consequence, non-absorbed quencher compound is undesirably discharged into the waste water. Moreover, the compounds of DE-A-2 448 293 tend to flocculate, which is disadvantageous for use in the "wet-end" (paper formation) part of the paper-making process.

Surprisingly, it has now been found that triazine-based ultra-violet absorption agents (UVAs), when used as quenchers in paper-making processes, provide better absorption on to the fibre, lower waste water contamination and lower influence on dispersion stability (lower tendency to flocculate), relative to the compounds of DE-A-2 448 293.

Accordingly, the present invention provides a process for the inhibition (quenching) of the effect of an anionic fluorescent whitening agents on a substrate, comprising treating the substrate with a triazine UVA compound.

One preferred class of triazine UV absorbers is that having the formula:

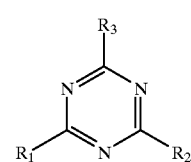

in which at least one of $R_1$, $R_2$ and $R_3$ is a radical of formula:

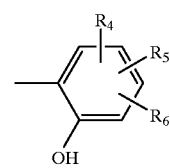

in which $R_4$, $R_5$ and $R_6$, independently, are hydrogen; $C_1$–$C_{12}$alkoxy; hydroxy; —O—$CH_2$—CO—NH—$CH_2$OH; $SO_3M$ in which M is hydrogen, sodium, potassium, ammonium, mono-, di-, tri- or tetra-$C_1$–$C_4$alkylammonium, mono-, di- or tri-$C_1$–$C_4$hydroxyalkylammonium or ammonium that is di- or tri-substituted by a mixture of $C_1$–$C_4$alkyl and $C_1$–$C_4$hydroxyalkyl groups; or

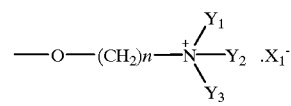

in which n is an integer from 2 to 6 and is preferably 2 or 3;

$Y_1$ and $Y_2$, independently, are $C_1$–$C_4$alkyl optionally substituted by halogen, cyano, hydroxy or $C_1$–$C_4$alkoxy or $Y_1$ and $Y_2$, together with the nitrogen atom to which they are each attached, form a 5–7 membered heterocyclic ring, preferably a morpholine, pyrrolidine, piperidine or hexamethyleneimine ring; $Y_3$ is hydrogen, $C_3$–$C_4$alkenyl or $C_1$–$C_4$alkyl optionally substituted by cyano, hydroxy or $C_1$–$C_4$alkoxy or $Y_1$, $Y_2$ and $Y_3$, together with the nitrogen atom to which they are each attached, form a pyridine or picoline ring; and $X_1^-$ is a colourless anion, preferably $CH_3OSO_3^-$ or $C_2H_5OSO_3^-$; and the remaining substituent(s) $R_1$, $R_2$ and $R_3$ are, independently, halogen, preferably chlorine, $C_1$–$C_{12}$alkoxy or phenyl, the phenyl substituent being optionally substituted by one or more of hydroxy, $C_1$–$C_{12}$-alkoxy, —O—$CH_2$—CO—NH—$CH_2$OH, $SO_3M$ in which M has its previous significance.

In the compounds of formula (1), $C_1$–$C_4$alkyl groups $Y_1$, $Y_2$ and $Y_3$ may be methyl, ethyl, n-propyl, isopropyl, n-butyl, isobutyl, tert.-butyl, methyl and ethyl being preferred.

$C_1$–$C_{12}$Alkoxy groups $R_1$, $R_2$, $R_3$, $R_4$, $R_5$ and $R_6$ may be, e.g., methoxy, ethoxy, n-propoxy, isopropoxy, n-butoxy, isobutoxy, tert.-butoxy, n-amyloxy, n-hexoxy, n-heptoxy, noctoxy, isooctoxy, n-nonoxy, n-decoxy, n-undecoxy or n-dodecoxy, methoxy and ethoxy being preferred.

The alkyl radicals in the mono-, di-, tri- or tetra-$C_1$–$C_4$alkylammonium groups M are preferably methyl. Mono-, di- or tri-$C_1$–$C_4$hydroxyalkylammonium groups M are preferably those derived from ethanolamine, di-ethanolamine or tri-ethanolamine. When M is ammonium that is di- or tri-substituted by a mixture of $C_1$–$C_4$alkyl and $C_1$–$C_4$hydroxyalkyl groups, it is preferably N-methyl-N-ethanolamine or N,N-dimethyl-N-ethanolamine. M is preferably, however, hydrogen or sodium.

Preferred compounds of formula (1) are those having the formulae:

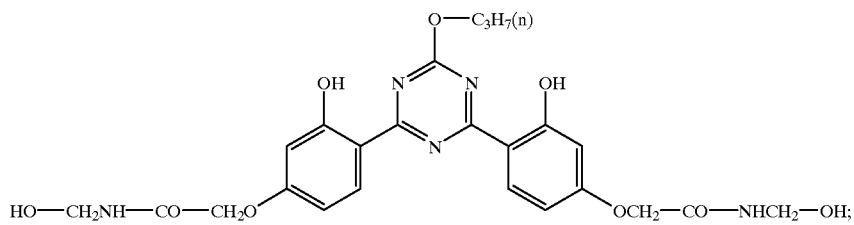

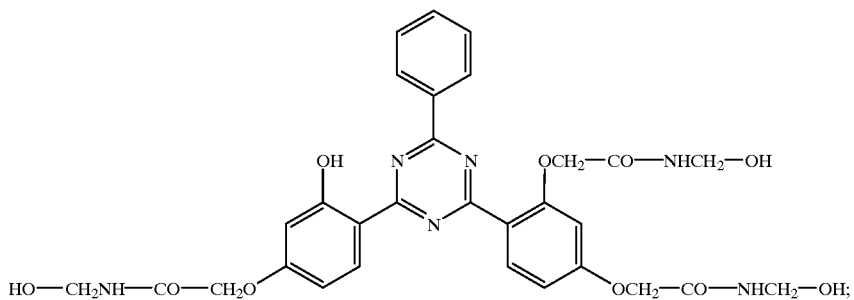

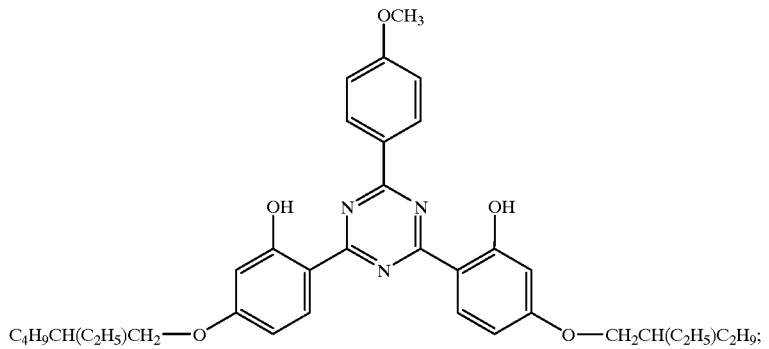

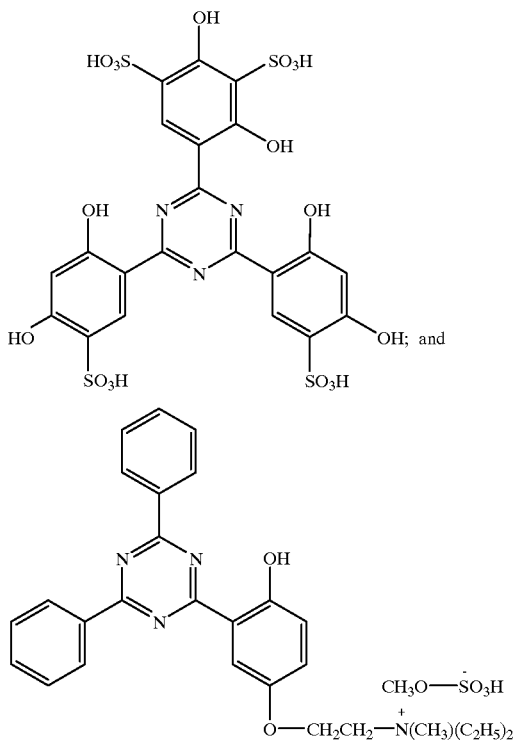

The compounds of formula (1) are known and may be prepared e.g. by the method described in U.S. Pat. Nos. 3,118,887 and 5,197,991.

A second preferred class of triazine UVAs is that having the formula:

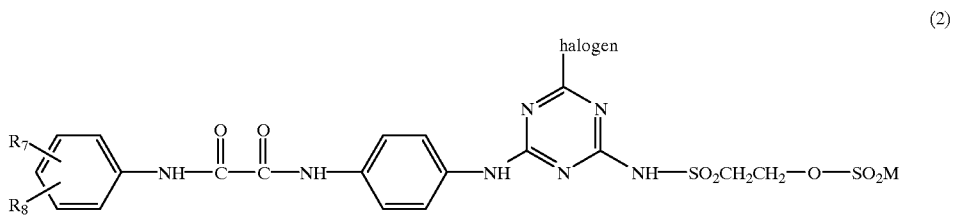

(2)

in which M has its previous significance and $R_7$ and $R_8$ are $C_1$–$C_{12}$-alkoxy or $SO_3M$ in which M has its previous significance. Preferably halogen is chlorine.

$C_1$–$C_{12}$Alkoxy groups $R_7$ and $R_8$ may be, e.g., methoxy, ethoxy, n-propoxy, isopropoxy, n-butoxy, isobutoxy, tert.-butoxy, n-amyloxy, n-hexoxy, n-heptoxy, n-octoxy, isooctoxy, n-nonoxy, n-decoxy, n-undecoxy or n-dodecoxy, methoxy and ethoxy being preferred.

A preferred compound of formula (2) is that having the formula:

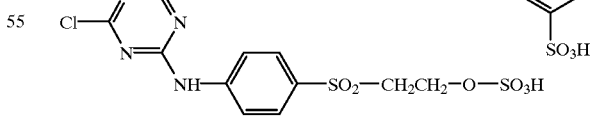

The compounds of formula (2) are known and may be prepared e.g. by the method described in U.S. Pat. Nos. 3,118,887 and 5,197,991.

A third preferred class of triazine UVAs is that having the formula:

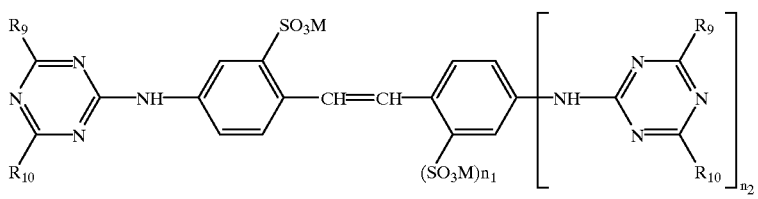

(3)

in which M has its previous significance; $n_1$ and $n_2$, independently, are 0 or 1, provided that if $n_1$ is 0, $n_2$ is 0;

$R_9$ is optionally substituted aryl or a group having the formula:

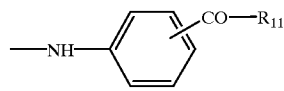

in which $R_{11}$ is optionally substituted alkyl or optionally substituted aryl; or, when $n_2$ is 0, $R_9$ may also be a group having one of the formulae:

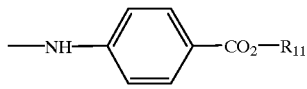

in which $R_{11}$ has its previous significance;

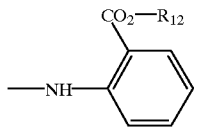

in which $R_{12}$ is M, optionally substituted alkyl or optionally substituted aryl;

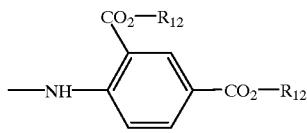

in which $R_{12}$ has its previous significance;

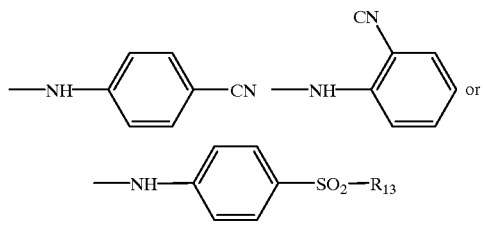

in which $R_{13}$ is hydrogen, optionally substituted alkyl or optionally substituted aryl; and $R_{10}$ is hydrogen, halogen, preferably chlorine, optionally substituted alkyl, optionally substituted aryl,

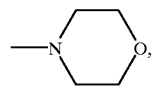

—OH, —$NH_2$, —$N(CH_2CH_2OH)_2$, —$N[CH_2CH(OH)CH_3]_2$, —NH—$R_{12}$, —$N(R_{12})_2$ or —$OR_{12}$, in which $R_{12}$ has its previous significance, or $R_{10}$ is an aminoacid residue from which a hydrogen atom on the amino group has been removed.

When one or more of $R_{10}$, $R_{11}$, $R_{12}$ and $R_{13}$ is optionally substituted alkyl, preferred unsubstituted alkyl groups $R_{10}$, $R_{11}$, $R_{12}$ and $R_{13}$ are $C_1$–$C_{12}$-, especially $C_1$–$C_4$-alkyl groups. The alkyl groups may be branched or unbranched and may be optionally substituted, e.g. by halogen such as fluorine, chlorine or bromine, by $C_1$–$C_4$-alkoxy such as methoxy or ethoxy, by phenyl or carboxyl, by $C_1$–$C_4$-alkoxycarbonyl such as acetyl, by a mono- or di-$C_1$–$C_4$alkylated amino group or by —$SO_3M$ in which M has its previous significance.

When one or more of $R_{10}$, $R_{11}$, $R_{12}$ and $R_{13}$ are optionally substituted aryl, they are preferably a phenyl or naphthyl group which may be substituted by $C_1$–$C_4$-alkyl, e.g. by methyl, ethyl, propyl, isopropyl, butyl, isobutyl, sec.-butyl or tert.-butyl, by $C_1$–$C_4$-alkoxy such as methoxy, ethoxy, propoxy, isopropoxy, butoxy, isobutoxy, sec.-butoxy or tert.-butoxy, by halogen such as fluorine, chlorine or bromine, by $C_2$–$C_5$-alkanoylamino, such as acetylamino, propionylamino or butyrylamino, by nitro, sulpho or by di-$C_1$–$C_4$alkylated amino.

Preferably, each of the aminoacid residues $R_{10}$ is the same. Examples of preferred aminoacid residues $R_{10}$ include those having the formula —NH—$CH(CO_2H)$—$R_{14}$ in which $R_{14}$ is hydrogen or a group having the formula —$CHR_{15}$ $R_{16}$ in which $R_{15}$ and $R_{16}$, independently, are hydrogen or $C_1$–$C_4$alkyl optionally substituted by one or two substituents selected from hydroxy, thio, methy(thio, amino, carboxy, sulfo, phenyl, 4-hydroxyphenyl, 3,5-diiodo-4-hydroxyphenyl, β-indolyl, β-imidazolyl and NH=C($NH_2$) NH—.

Specific examples of aminoacids from which such preferred aminoacid residues $R_{10}$ are derived include glycine, alanine, sarcosine, serine, cysteine, phenylalanine, tyrosine (4-hydroxyphenylalanine), diiodotyrosine, tryptophan (β-indolylalanine), histidine ((β-imidazolylalanine), α-aminobutyric acid, methionine, valine (α-aminoisovaleric acid), norvaline, leucine (α-aminoisocaproic acid), isoleucine (α-amino-β-methylvaleric acid), norleucine (α-amino-n-caproic acid), arginine, ornithine (α,δ-diaminovaleric acid), lysine (α,ε-diaminocaproic acid), aspartic acid (aminosuccinic acid), glutamic acid (α-aminoglutaric acid), threonine, hydroxyglutamic acid and taurine, as well as mixtures and optical isomers thereof. Of these aminoacids from which such preferred aminoacid residues $R_{10}$ are derived, glutamic acid and aspartic acid are particularly preferred.

A further preferred example of an aminoacid from which an aminoacid residue $R_{10}$ may be derived is iminodiacetic acid.

Other, less preferred examples of aminoacids from which aminoacid residues $R_{10}$ may be derived include cystine, lanthionine, proline and hydroxyproline.

In each of the compounds of formula (3) it is preferred that they are used in neutral form, i.e. that M is other than hydrogen, preferably a cation formed from an alkali metal, in particular sodium, or from an amine.

In the compounds of formula (3), preferably $R_9$ is phenyl, methylphenyl, dimethylphenyl or a group of formula:

in which $R_{11}$ has its previous significance and is preferably $C_1$–$C_4$-alkyl, especially methyl or ethyl; and preferably $R_{10}$ is phenyl, methylphenyl, dimethylphenyl, —$NH_2$, Cl, —$N(CH_2CH_2OH)_2$ or —$N[CH_2CH(OH)CH_3]_2$.
Preferred compounds of formula (3) are those having the formula:

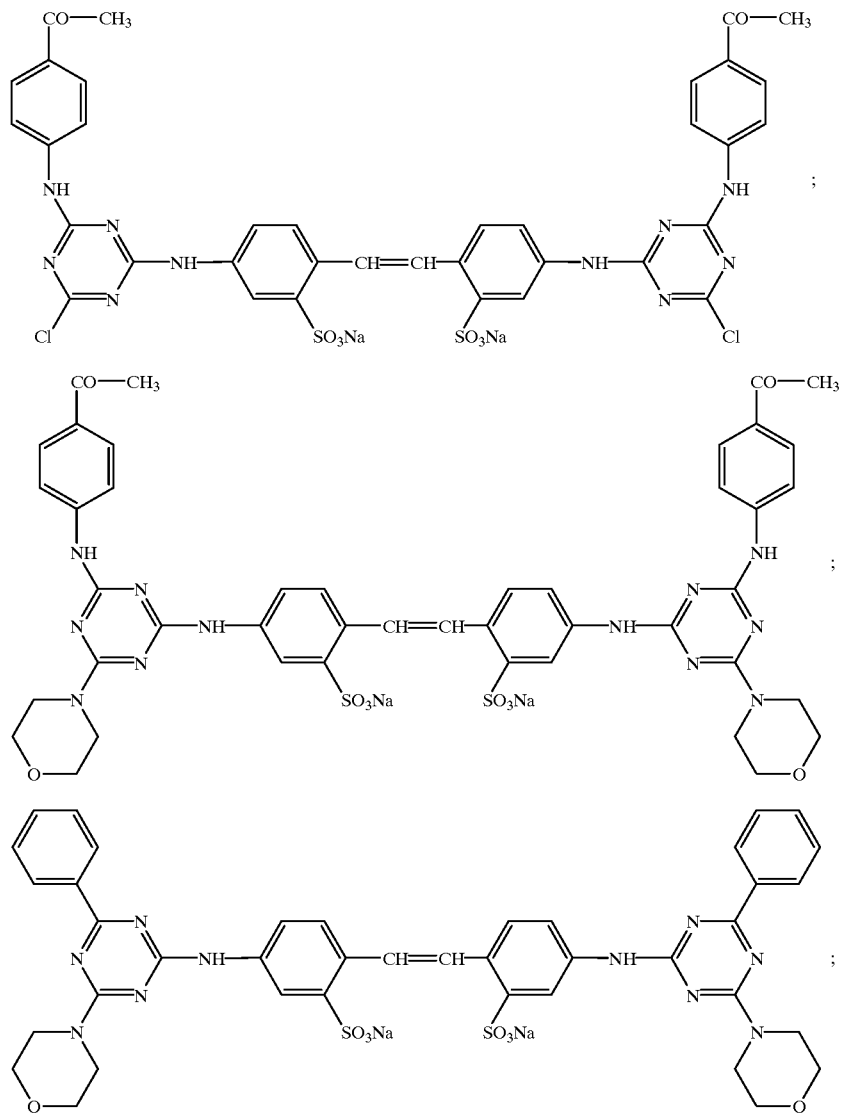

-continued
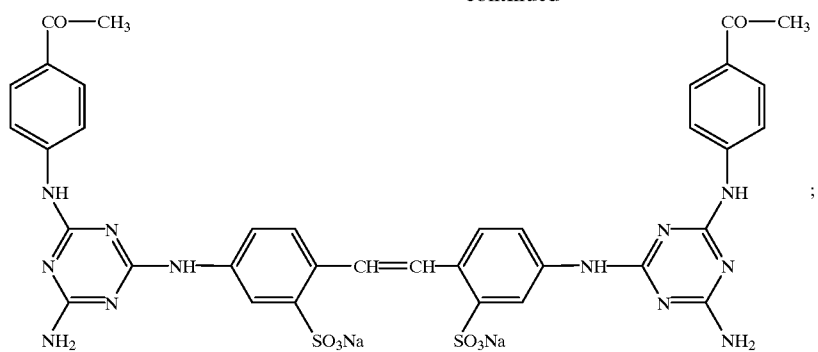
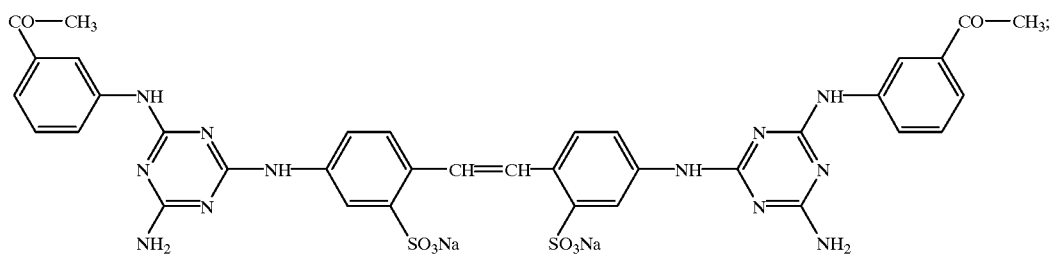
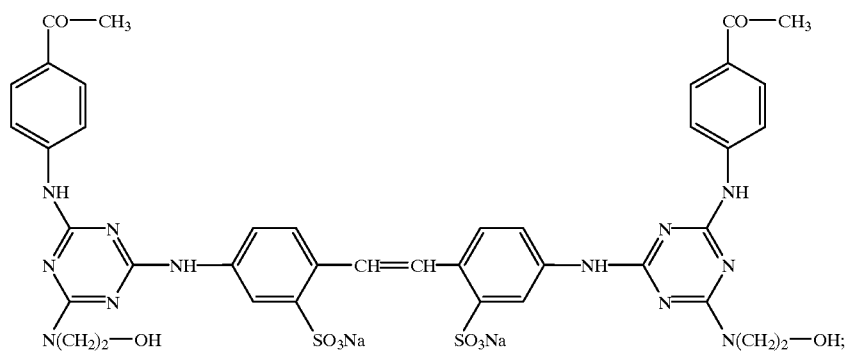
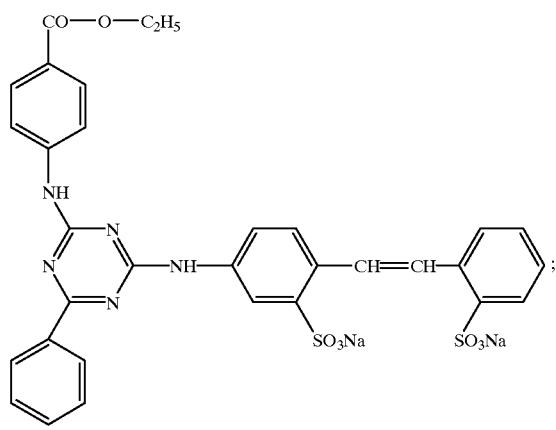
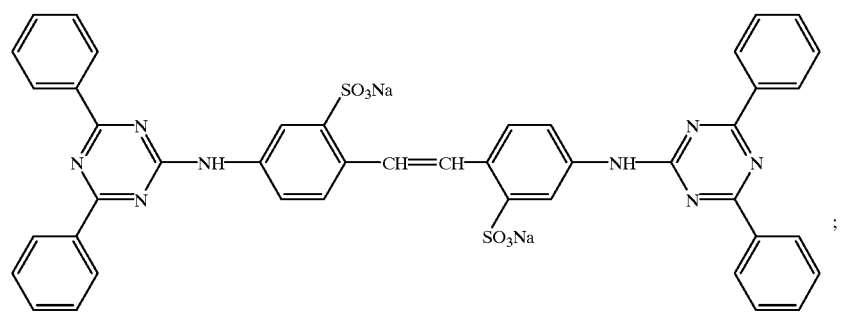

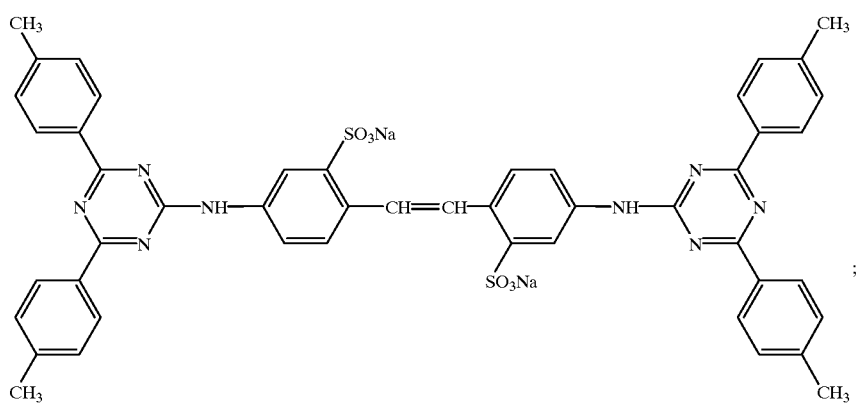
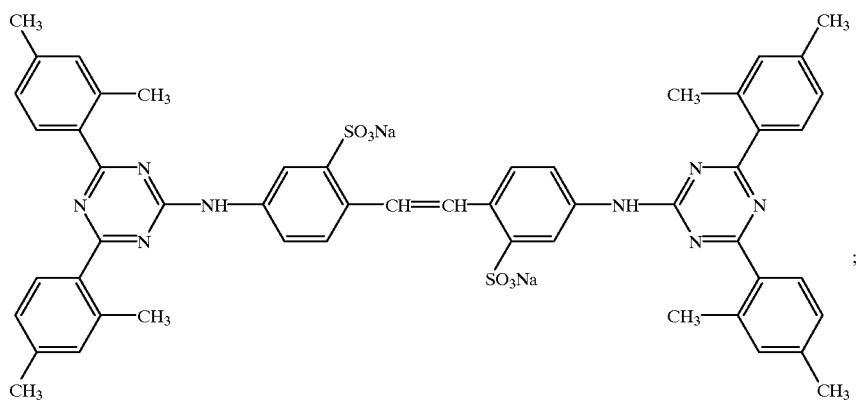
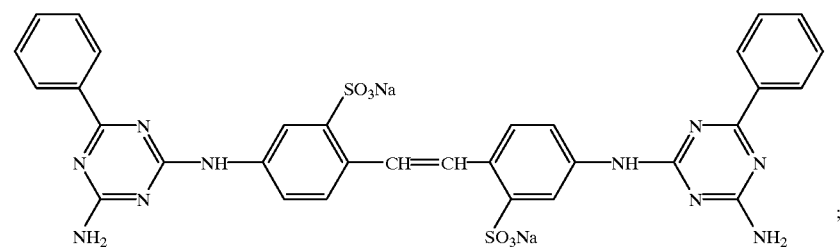
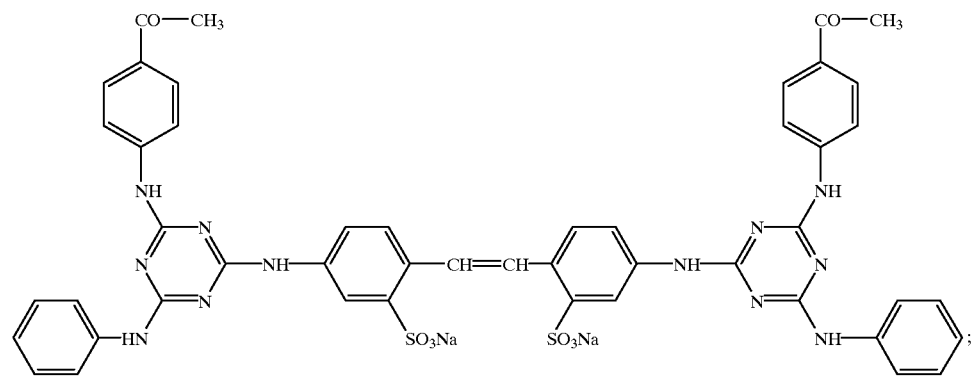

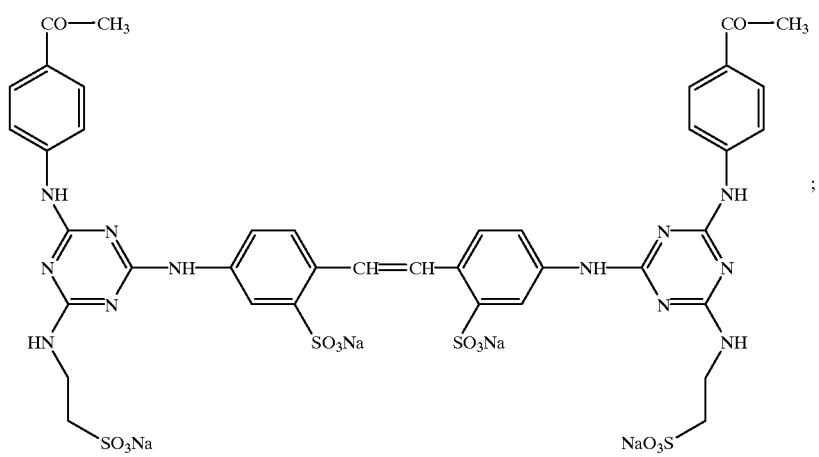
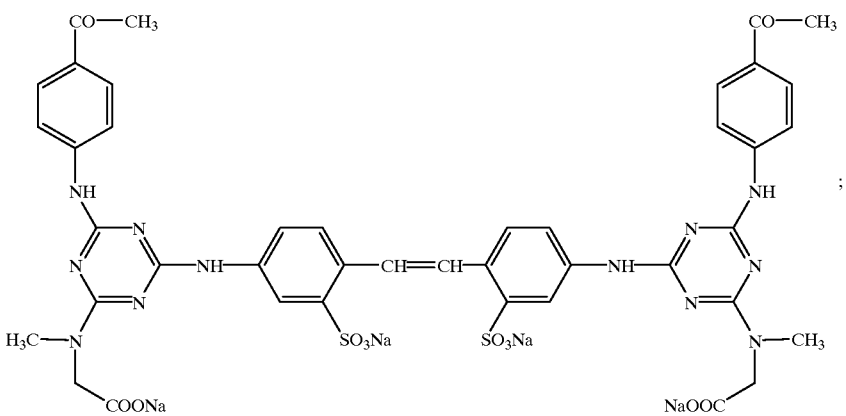
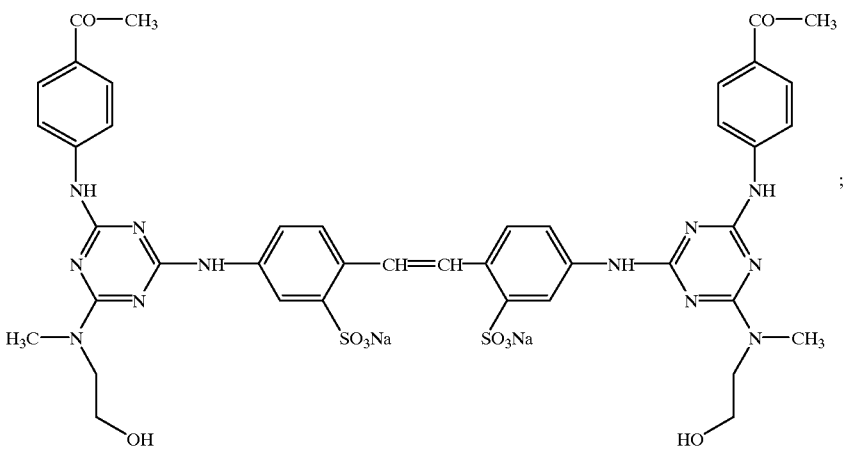

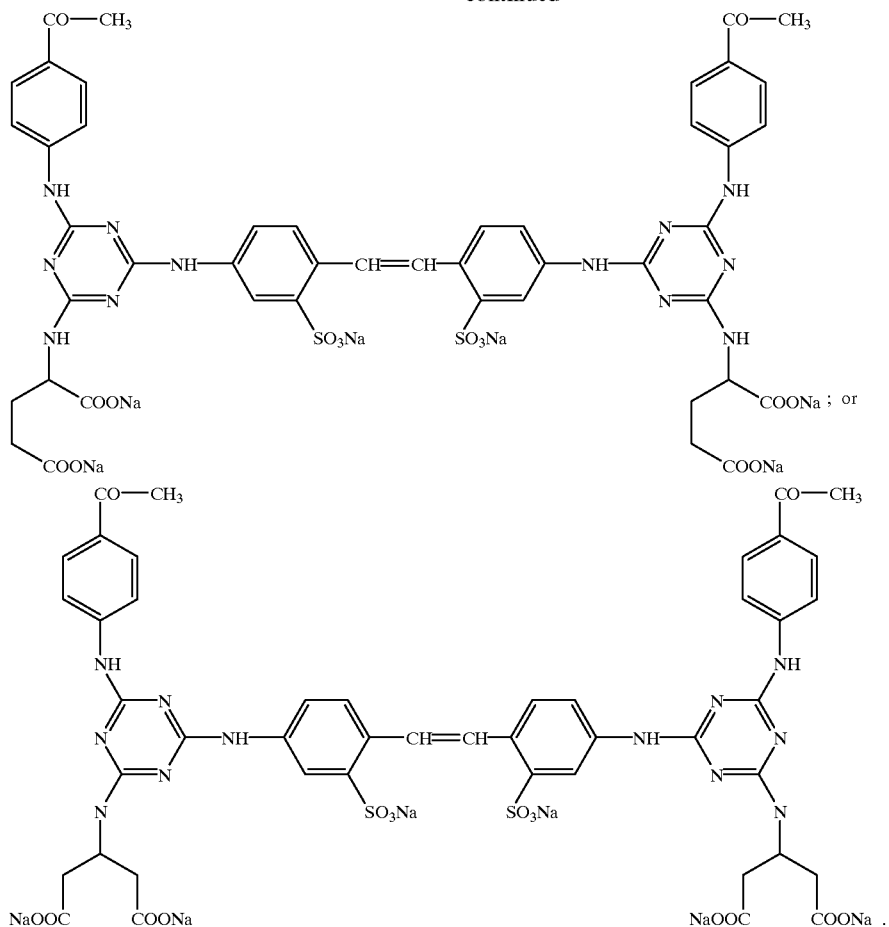

The compounds of formula (3) may be produced by reacting, under known reaction conditions, cyanuric chloride, successively, in any desired sequence, with each of an aminostilbene-sulfonic acid, an amino compound capable of introducing a group $R_9$ and a compound capable of introducing a group $R_{10}$, in which $R_9$ and $R_{10}$ each have their previous significance. Unsymmetrical compounds of formula (3), namely those in which $n_2$ is zero, may be produced by the method described in GB-A-2,298,422.

The starting materials are known compounds which are readily available.

Most of the compounds of formula (3) are known. Those compounds of formula (3), however, in which $R_9$ is optionally substituted aryl and $R_{10}$, M, $n_1$ and $n_2$ have their previous significance, are believed to be new compounds and, as such, form a further aspect of the present invention.

The new compounds of formula (3) may be produced from cyanuric chloride, as described above, but are preferably produced by using the appropriate intermediate selected from 2-chloro-4,6-diphenyl-1,3,5-triazine [produced according to the method of A. Ostrogovich; Chemiker Ztg. 36 (1912) 739], 2-amino-4-chloro-6-phenyl-1,3,5-triazine [produced according to the method described by H. K. Reimschuessel, N. T. McDevitt; J.Am.Chem.Soc. 82 (1960) 3756–3762] or the new intermediate 2-chloro-4-N-morpholino-6-phenyl-1,3,5-triazine. The latter new intermediate may be obtained by reacting 2,4-dichloro-6-phenyl-1, 3,5-triazine with morpholine under known reaction conditions.

The triazine-based ultra-violet absorption agents used as quencher compounds according to the process of the present invention are preferably used in an amount ranging from 0.5 to 50 times the amount of fluorescent whitening agent present in the substrate to be treated.

The following Examples further illustrate the present invention.

EXAMPLES 1 to 5

5 g of dry sulfite pulp, consisting of a 1:1 mixture of bleached beech fibres and bleached spruce fibres (Schopper-Riegler), are suspended in 150 mls of water. 5% of a calcium carbonate filler is then added to the fibre suspension, followed by 0.2% of active substance, each based on the weight of fibre, of the fluorescent whitening agent having the formula:

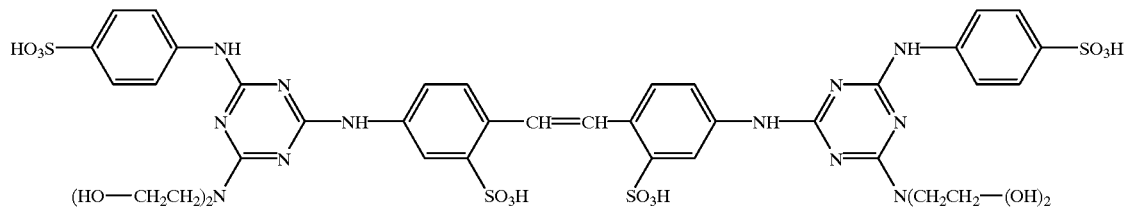
(as the diethanolamine salt). The mixture is then stirred at room temperature for 15 minutes.
There are then added 25 mls of a solution, in a dimethylsulfoxide/water (20:80) mixture, of one of the following quencher test compounds, to give respective pulp suspensions containing 0.2% by weight, based on the weight of pulp, of the test quencher compound:
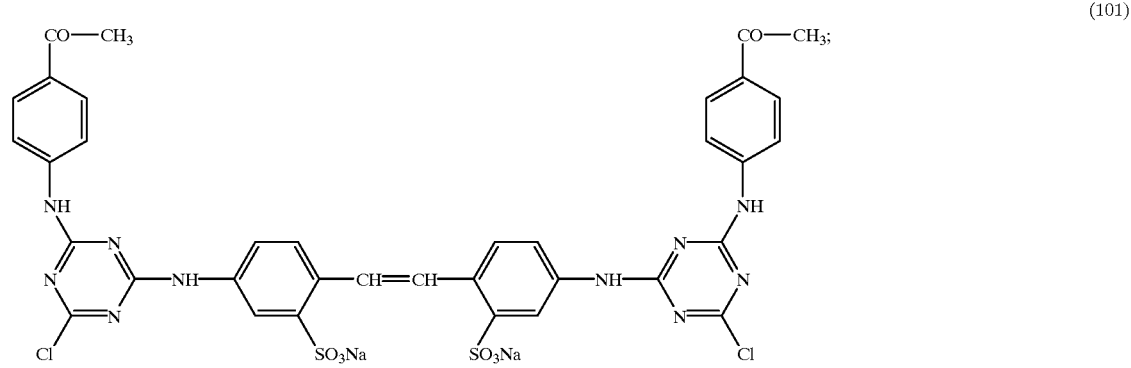
(101)
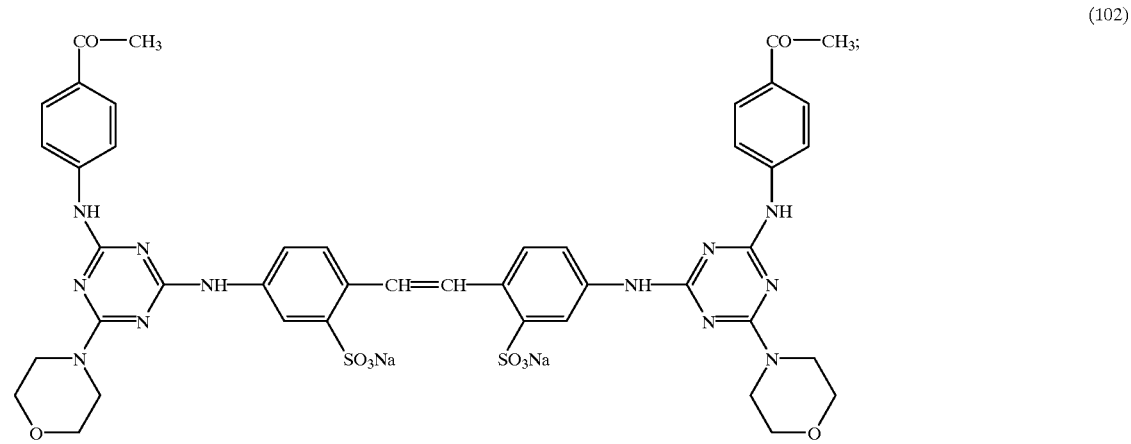
(102)
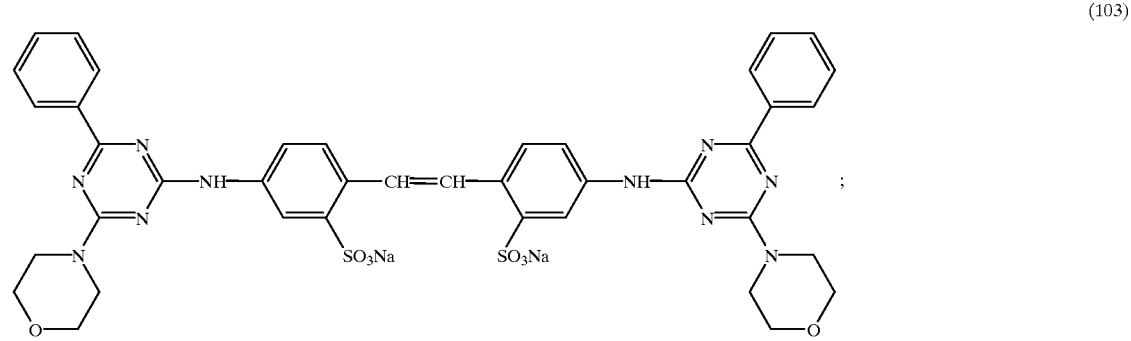
(103)

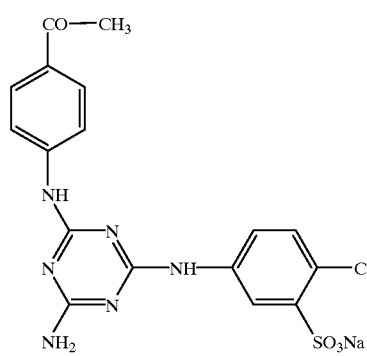
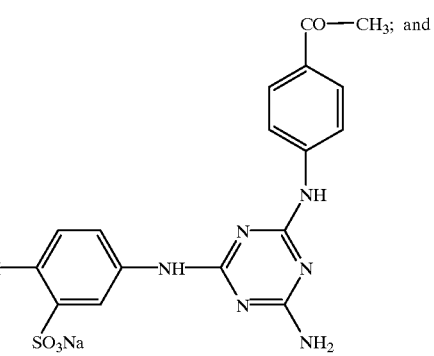

(104)

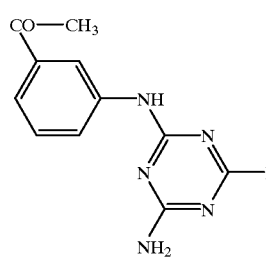
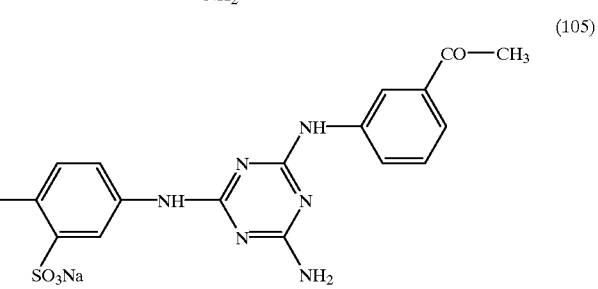

(105)

The respective test quencher compounds are then stirred for an additional 15 minutes at room temperature in order to allow them to exert their effect.

Paper sheets are then formed from the respective suspensions (diluted to a consistency of 0.2% with water of 10° German hardness) using a Rapid-Köthen apparatus. After drying the finished paper sheet for 15 minutes, a dry paper sheet having a weight per unit area of 160 g/m².

For the purpose of comparison, a paper sheet is produced in the same way from the basic pulp suspension containing the fluorescent whitening agent but no test quencher compound.

24 Hours after the production of the respective paper sheets, the Ganz whiteness and the fluorescence (ISO) are determined using the Spektaflash device. The Ganz method is described in detail in the Ciba-Geigy Review, 1973/1, and also in the article "Whiteness Measurement", ISCC Conference on Fluorescence and the Colorimetry of Fluorescent Materials, Williamsburg, February 1972, published in the Journal of Color and Appearance, 1, No.5 (1972).

The results obtained are set out in the following Table.

TABLE

| Example | Test Quencher | Ganz Whiteness | ISO Fluorescence |
|---------|---------------|----------------|------------------|
| control | none | 187.4 | 17.8 |
| 1 | 101 | 142.0 | 13.8 |
| 2 | 102 | 126.8 | 11.9 |
| 3 | 103 | 87.5 | 7.4 |
| 4 | 104 | 78.5 | 8.7 |
| 5 | 105 | 107.5 | 9.5 |

The results in the Table indicate the significant reduction in whiteness and fluorescence of paper treated with a quencher compound according to the present invention.

EXAMPLE 6

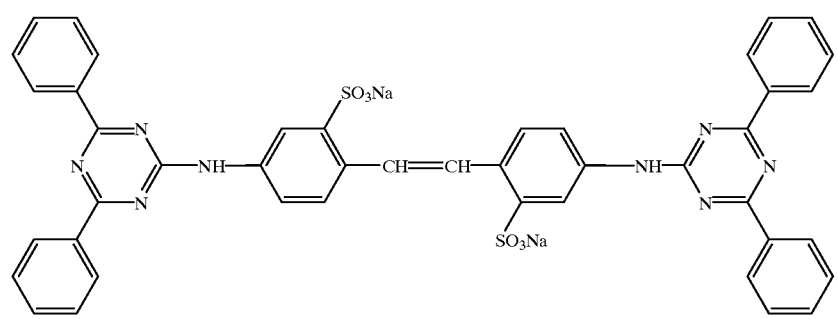

(106)

4.32 g of 4,4'-diaminostilbene-2,2'-disulfonic acid are stirred in 200 mls of dimethylformamide and heated to 55° C. There are then added to this mixture 4.32 g of 2-chloro-4,6-diphenyl-1,3,5-triazine [produced according to the method of A. Ostrogovich; Chemiker Ztg. 36 (1912) 739] and 2.27 g of sodium carbonate and the resulting mixture is heated to 105–110° C. for 28 hours. After cooling, the yellow suspension so obtained is rotated, boiled with 150 mls of a methanol/methylethylketone/water mixture, alowed to cool and then filtered. After drying in vacuum, there are obtained 5.45 g of a yellow powder of formula (106) characterized as follows:

$\lambda_{max}$ 370 nm/ $\epsilon$ 54000 (DMF):

$^1$H-NMR (DMSO-d$_6$): δ(in ppm)=10.42 (s, 2H, NH—), 8.75 (d, 2H, aromatic), 8.65 (d, 8H, aromatic), 8.14 (s, 2H, —CH=CH—), 7.89 (dd, 2H, aromatic), 7.71 (d, 2H, aromatic), 7.68–7.56 (m, 12H, aromatic).

EXAMPLE 7

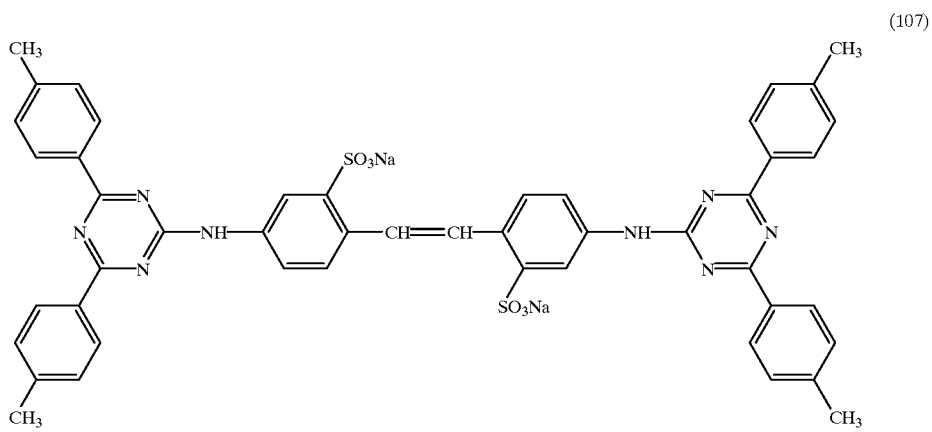
(107)

Using an analogous procedure to that described in Example 6, the compound of formula (107) is obtained and is characterized as follows:

$\lambda_{max}$ 370 nm/ $\epsilon$ 52900 (DMF):

$^1$H-NMR (DMSO-d$_6$): δ(in ppm)=10.42 (s, 2H, NH—), 8.76 (d, 2H, aromatic), 8.55 (d, 8H, aromatic), 8.14 (s, 2H, —CH=CH—), 7.85 (dd, 2H, aromatic), 7.70 (d, 2H, aromatic), 7.43 (d, 8H, aromatic), 2.45 (s, 12H, —CH$_3$).

EXAMPLE 8

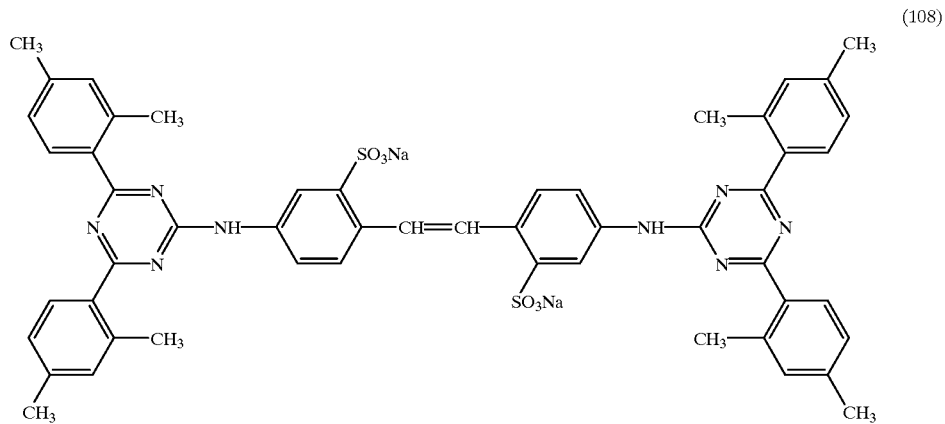
(108)

Using an analogous procedure to that described in Example 6, the compound of formula (108) is obtained and is characterized as follows:

λ$_{max}$ 364 nm/ ε 52900 (DMF):

$^1$H-NMR (DMSO-d$_6$): δ(in ppm)=10.31 (s, 2H, NH—), 8.33 (d, 2H, aromatic), 8.08 (s, 2H, —CH=CH—), 8.02 (d, 4H, aromatic), 7.90 (dd, 2H, aromatic), 7.63 (d, 2H, aromatic), 7.21 (d, 4H, aromatic), 7.18 (s, 4H, aromatic), 2.66 (s, 12H, —CH$_3$), 2.36 (s, 12H, —CH$_3$).

EXAMPLE 9

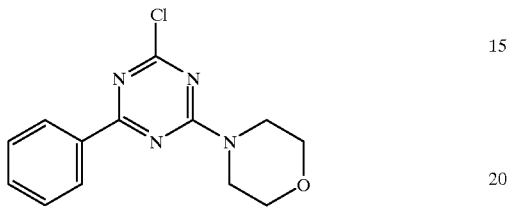

109A

A) 15.82 g of 2,4-dichloro-6-phenyl-1,3,5-triazine are stirred at 20° C. into 200 mls of acetone and treated with 6.2 mls of morpholine and 9.4 mls of collidine. The mixture is stirred for 6 hours, made up to 1000 mls with cooled water and acidified with concentrated HCl. After stirring for 20 minutes, the suspension is filtered with suction, washed with deionised water and dried over phosphorus pentoxide. In this way, there are obtained 18.21 g of a beige powder having the formula (109A) and being characterized as follows:

$^1$H-NMR (acetone-d$_6$): δ(in ppm)=8.41 (d, 2H, aromatic), 7.62 (t, 1H, aromatic), 7.52 (t, 2H, aromatic), 4.05 (t, 2H, —CH$_2$—), 3.87 (t, 2H, —CH$_2$—), 3.80-3.72 (m, 4H, —CH$_2$—).

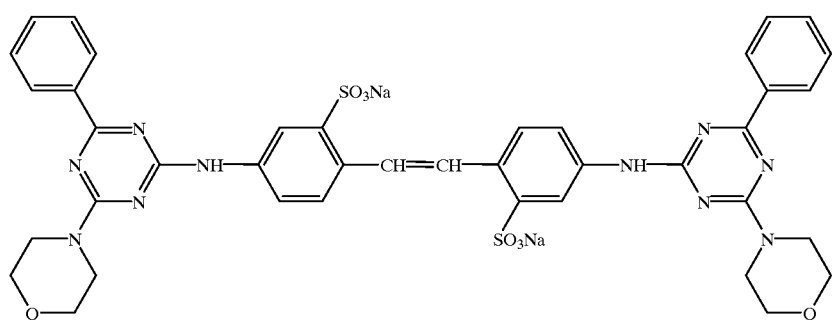

(103)

B) Using an analogous procedure to that described in Example 6, the compound of formula (109A) is reacted with 4,4-diaminostilbene-2,2'-isulfonic acid and the compound of formula (103) is obtained and is characterized as follows:

λ$_{max}$ 363 nm/ ε 55557 (DMF/water):

$^1$H-NMR (D$_2$O): δ(in ppm)=8.56 (s, 2H, aromatic), 8.27 (d, 4H, aromatic), 7.84 (s, 2H, —CH=CH—), 7.73 (d, 2H, aromatic), 7.63 (t, 2H, aromatic), 7.59–7.48 (m, 6H, aromatic), 3.89 (s, 8H, —CH$_2$—), 3.80 (s, 8H, —CH$_2$—).

EXAMPLE 10

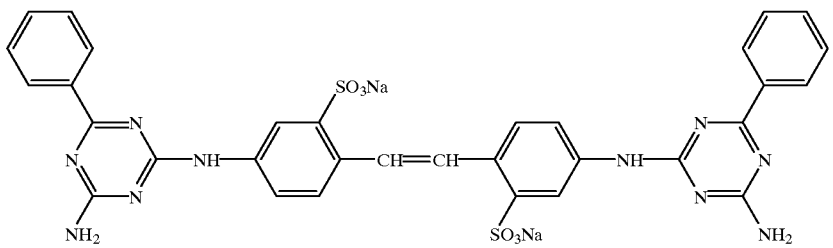
(110)

Using an analogous procedure to that described in Example 6, 2-amino-4-chloro-6-phenyl-1,3,5-triazine [produced according to the method described by H. K. Reimschuessel, N. T. McDevitt; J.Am.Chem.Soc. 82 (1960) 3756–3762] is reacted with 4,4'-diaminostilbene-2,2'-disultonic acid and the compound of formula (110) is obtained and is characterized as follows:

$\lambda_{max}$ 360 nm/ $\epsilon$ 45366 (DMF/water):

$^1$H-NMR (MeOH-d$_4$): δ(in ppm)=8.65 (s, 2H, aromatic), 8.47 (d, 4H, aromatic), 8.17 (s, 2H, —CH=CH—), 7.96 (d, 2H, aromatic), 7.85 (dd, 2H, aromatic), 7.63–7.52 (m, 6H, aromatic).

EXAMPLE 11

The reaction mixture is heated to 130° C. in an oilbath and held at this temperature for 4 hours. After a short time, the free acid version of the salt compound (111) crystallises out. After filtration with suction, the filtercake, dissolved in methanol, is converted into the di-sodium salt of formula (111) using sodium methylate. After filtration with suction, washing with water and drying, there are obtained 4.0 g (91% theory) of the di-sodium salt of formula (111).

Elemental analysis of the compound having the formula (111) and having the empirical formula $C_{48}H_{38}N_{12}Na_2O_8S_2$. 11.0 $H_2O$ gives:

Req.% C 47.29; H 4.96; N 13.78; S 5.26; $H_2O$ 16.24.
Found % C 47.05; H 4.96; N 13.87; S 5.28; $H_2O$ 15.99.

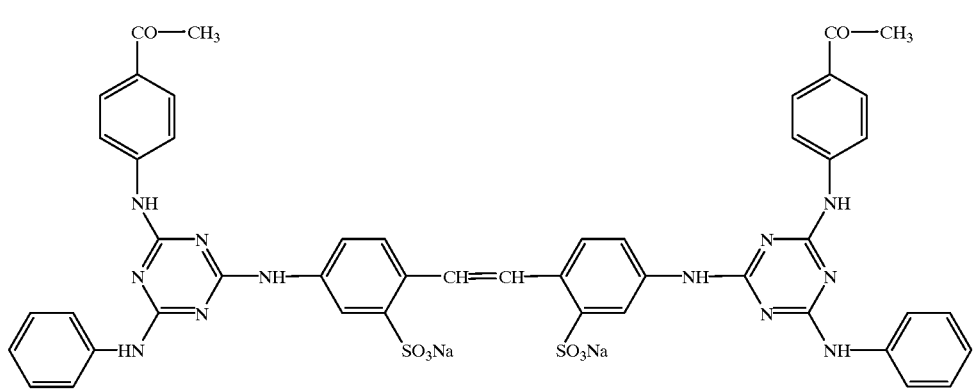
(111)

1.2 g of 4-aminoacetophenone are dissolved in 30 ml of methylcellosolve. To this solution are then added 3.3 g of the compound (91% purity) having the formula:

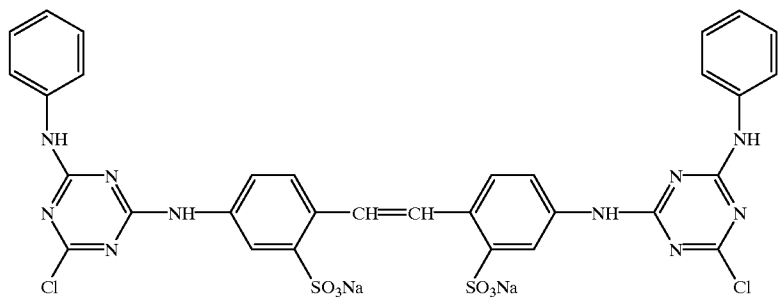

EXAMPLE 12

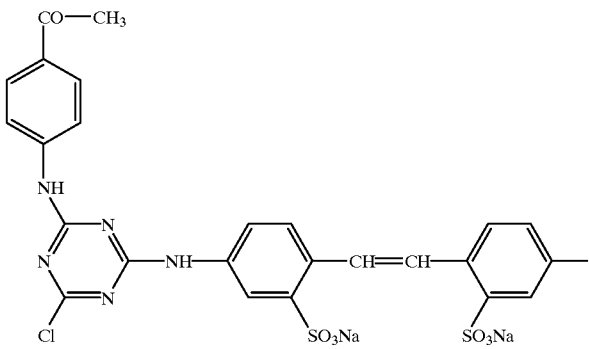

(101)

18.81 g of cyanuric chloride (98% purity) are dissolved in 95 ml of acetone and poured on to 100 g of a mixture of ice and water. Over 30 minutes, a solution of 18.5 g of of diaminostilbene-di-sulfonic acid (100% purity) is added, dropwise, into 320 g of a mixture of ice and water at a temperature in the range of from −5° C. to 0° C. Finally, over 15 minutes, 50 ml of a 1 molar soda solution are added, dropwise, at this temperature, and the whole is stirred for a further 1 hour. 13.5 g of 4-aminoacetophenone are added and the mixture is heated to 50° C., over 90 minutes. During this procedure, the pH of the reaction mixture is held at 7–8 by the addition of sodium carbonate. In order to complete the reaction, the acetone is distilled off until the temperature of the reaction mixture has reached 66° C. The precipitated deposit is filtered warm with suction, washed with dilute aqueous sodium chloride (2%) and then with 300 ml of cold water. After drying, there remain 44.8 g (88% theory) of the compound of formula (101).

Elemental analysis of the compound having the formula (101) and having the empirical formula $C_{36}H_{26}N_{10}O_8Cl_2S_2Na_2$. 6.0 $H_2O$ gives:

Req.% C 42.57; H 3.77; N 13.79. Found % C 42.59; H 3.85; N 13.74.

EXAMPLE 13

5 g of the compound of formula (101) obtained in Example 12 are suspended in 100 ml of water. 1.3 g of taurine are added and the reaction mixture is heated to 90° C. and the pH is held at 9–10 using sodium carbonate. The reactants are allowed to further react at this pH and temperature for 15 hours. Finally, the reaction mixture is concentrated and the compound (113) is precipitated with acetone. After filtration with suction, washing with acetone and drying, there remain 5.9 g (81% theory) of the compound (113).

Elemental analysis of the compound having the formula (113) and having the empirical formula $C_{40}H_{36}N_{12}Na_4O_{14}S_4$. 0.66 NaCl. 16.5 $H_2O$ gives:

Req.% C 32.8; H 4.74; N 11.47; S 8.75; Cl 1.60; Na 7.32. Found % C 32.7; H 4.7; N 11.5; S 9.1; Cl 1.6; Na 7.4.

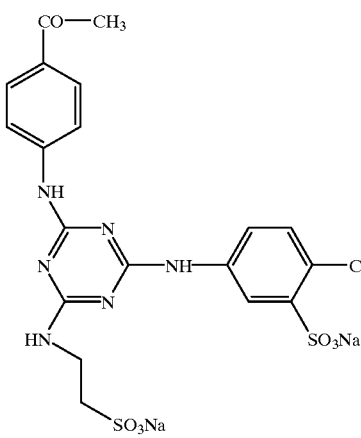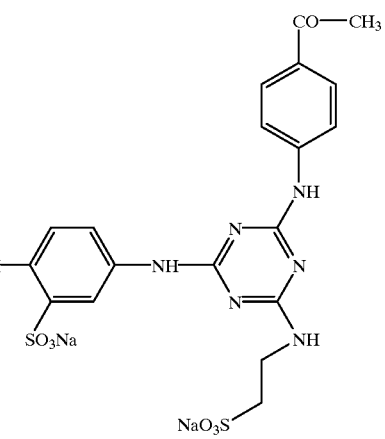

(113)

EXAMPLE 14

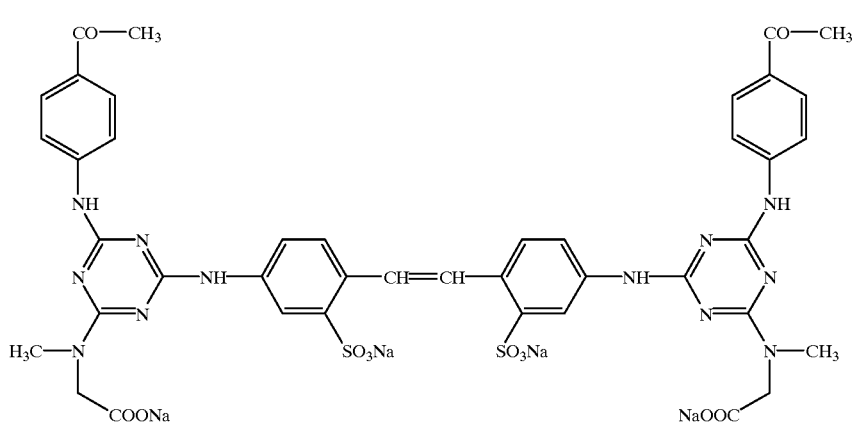

(114)

Using an analogous procedure to that described in Example 13, compound (114) is produced by reacting the compound (101) with 0.9 g of sarcosine instead of taurine. The reaction is complete after 6 hours and the yield of the compound (114) is 93% of theory.

Elemental analysis of the compound having the formula (114) and having the empirical formula $C_{42}H_{36}N_{12}Na_4O_{12}S_2$ 15 $H_2O$ gives:

Req.% C 38.02; H 5.01; N 12.66. Found % C 38.10; H 4.87; N 12.65.

EXAMPLE 15

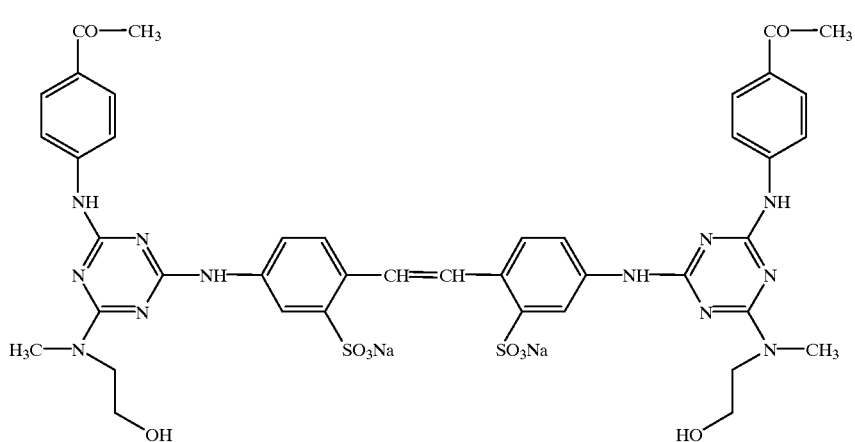

(115)

Using an analogous procedure to that described in Example 13, compound (115) is produced by reacting the compound (101) with N-methyl-ethanolamine instead of taurine. The reaction is complete after 6.5 hours and the yield of the compound (115) is 81% of theory.

The material analyzed was partly present as the N-methyl-ethanolamine salt.

Elemental analysis of the compound having the formula (115) and having the empirical formula $C_{42}H_{42}N_{12}Na_2O_{10}S_2$. 0.6 N-methyl-ethanolamine. 5 $H_2O$ gives:

Req.% C 47.0; H 5.02; N 15.78; S 5.73. Found % C 46.75; H 4.92; N 15.46; S 5.71

EXAMPLE 16

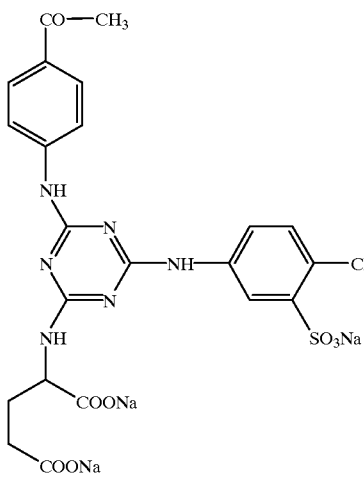
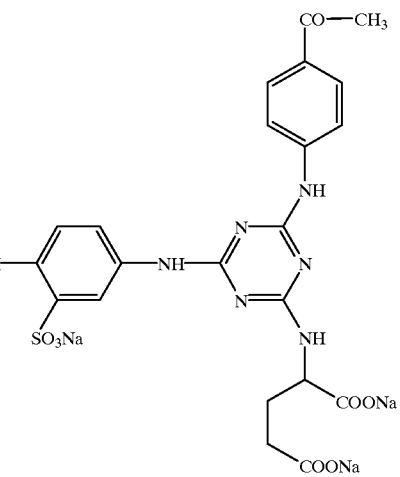

(116)

10 g of the compound of formula (101) are reacted with 5.8 g of L-glutamic acid in a 6:9 by weight mixture of water and methylcellosolve at 120° C. in an oil bath, the pH being held at 8–9 by the addition of sodium carbonate. After 6 hours, the reaction is complete. The reaction mixture is dropped into acetone acidified with HCl, whereupon the compound of formula (116) precipitates out as the free acid. After filtration with suction and washing with acetone-water, the filtercake is converted into the corresponding hexasodium salt by the addition of the calculated amount of aqueous sodium hydroxide, and evaporation to dryness. The yield is 90% of theory.

Eiemental analysis of the compound having the formula (116) and having the empirical formula $C_{46}H_{38}N_{12}Na_6O_{10}S_2$. 0.3 NaCl. 17 $H_2O$ gives:

Req.% C 35.9; H 4.71; N 10.92; S 4.16. Found % C 36.0; H 4.7; N 10.9; S 4.1.

EXAMPLE 17

The compound of formula (117) is obtained in a yield of 87% of theory using the procedure described in Example 16, except that the L-glutamic acid is replaced by iminodiacetic acid.

Elemental analysis of the compound having the formula (117) and having the empirical formula $C_{44}H_{34}N_{12}Na_6O_{16}S_2$. 0.8 NaCl. 15 $H_2O$ gives:

Req.% C 35.1; H 4.28; N 11.16; S 4.26. Found % C 35.0; H 4.3; N 11.2; S 4.4.

EXAMPLES 18 to 26

The activity as quenchers of various triazine-based UVAs used according to the present invention is investigated as follows. The fibre suspension used is an industrially produced suspension consisting predominantly of eucalyptus pulp taken from the pulp circulating in a paper machine. Since the test fibre suspension contains only a minor amount of fluorescent whitening agent, there is added to the fibre suspension 0.1% by weight of active substance of a commercial paper fluorescent whitening agent based on a substituted tetrasulfostilbene. After a further 24 hours has elapsed, to enable the added fluorescent whitening agent to exert its effect, the test quencher compound is added, at a level of 0.8% by weight of active substance, to the fibre suspension in a consistency of 1% by weight. After 15 minutes exhaustion time, a paper sheet is formed using the

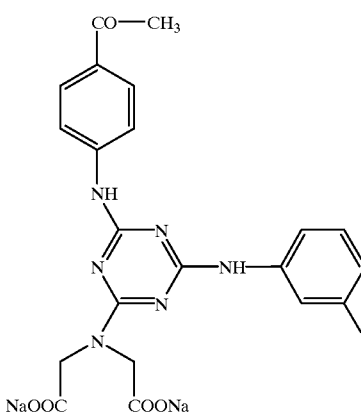
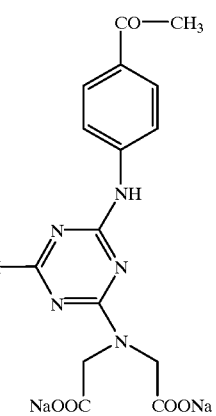

(117)

Rapid Kothen system and the sheet is dried. The dried sheet is then exposed to xenon light (Spektraflash SF 500) and the fluorescence of the sheet is determined, firstly using a UV barrier filter (420 nm) and then without the use of the UV barrier filter. The difference between the two measurements at 440 nm is designated as the fluorescence (F 440).

The test quencher compounds have the formula:

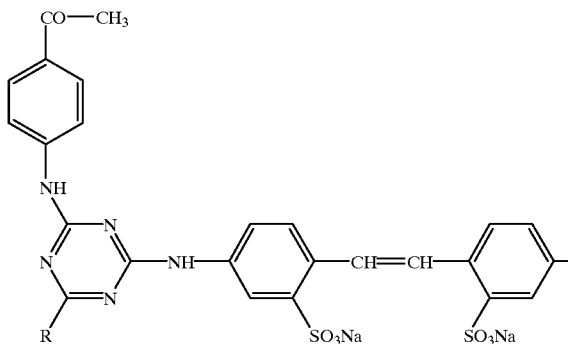

The test results obtained, using compounds having various substituents R, are set out in the following Table.

TABLE

| Example | R | F 440 |
|---|---|---|
| — | control (no quencher) | 31 |
| 18 | $NH_2$ (compound 104) | 9 |
| 19 | anilino (NH-phenyl) (compound 111) | 10 |
| 20 | $NH\text{-}(CH_2)_2\text{-}OCH_3$ | 9 |
| 21 | $O\text{-}(CH_2)_2\text{-}CH_3$ | 18 |
| 22 | $NH\text{-}(CH_2)_5\text{-}COOH$ | 12 |
| 23 | $N(CH_3)(CH_2COOH)$ (compound 114) | 11 |
| 24 | $NH\text{-}(CH_2)_2\text{-}SO_3H$ (compound 113) | 12 |
| 25 | $N(CH_3)\text{-}(CH_2)_2\text{-}OH$ (compound 115) | 10 |
| 26 | $N(_2H_5)\text{-}(CH_2)_2\text{-}OH$ | 11 |

Since the higher the value of F 440, the higher the fluorescence, it will be noted that the test compounds significantly reduce (quench) the fluorescence, relative to the control experiment.

What is claimed is:

1. A process for the inhibition (quenching) of the effect of an anionic fluorescent whitening agent on a substrate, comprising treating the substrate with a triazine UVA compound of the formula (3)

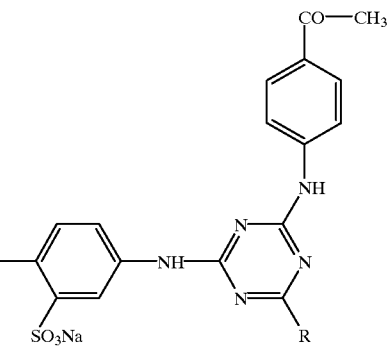

in which M is hydrogen, sodium, potassium, ammonium, mono-, di-, tri- or tetra-$C_1$–$C_4$alkylammonium, mono-, di- or tri-$C_1$–$C_4$hydroxyalkylammonium or ammonium that is di- or tri-substituted by a mixture of $C_1$–$C_4$alkyl and $C_1$–$C_4$hydroxyalkyl groups;

$n_1$ and $n_2$, independently, are 0 or 1, provided that if $n_1$ is 0, $n_2$ is 0;

$R_9$ is optionally substituted aryl or a group having the formula

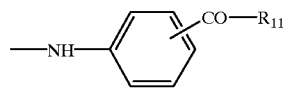

in which $R_{11}$ is optionally substituted alkyl or optionally substituted aryl;

or, when $n_2$ is 0, $R_9$ may also be a group having one of the formulae:

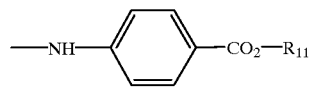

in which $R_{11}$ is optionally substituted alkyl or optionally substituted aryl;

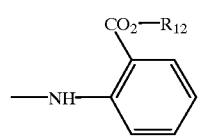

in which $R_{12}$ is M, optionally substituted alkyl or optionally substituted aryl;

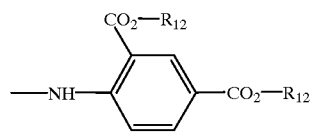

in which $R_{12}$ has its previous significance;

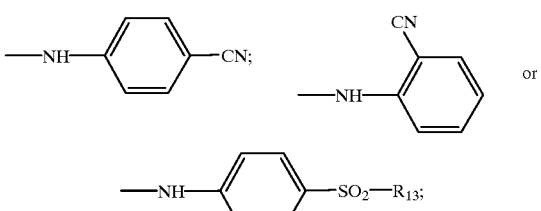

in which $R_{13}$ is hydrogen, optionally substituted alkyl or optionally substituted aryl; and $R_{10}$ is hydrogen, halogen, optionally substituted alkyl, optionally substituted aryl,

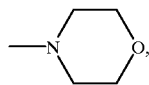

—$NH_2$, —$N(CH_2CH_2OH)_2$, —$N[CH_2CH(OH)CH_3]_2$, —NH—$R_{12}$, —$N(R_{12})_2$ or —$OR_{12}$, in which $R_{12}$ has its previous significance,
or $R_{10}$ is an aminoacid residue from which a hydrogen atom on the amino group has been removed;
or with a triazine UVA compound of formula

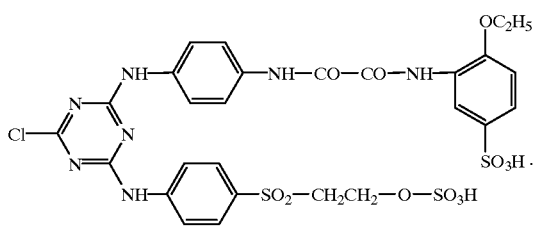

2. A process according to claim 1 in which the triazine UVA compound has the formula:

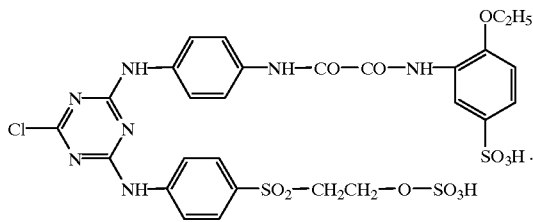

3. A process according to claim 1 in which $R_{10}$ is an aminoacid residue having the formula —NH—CH($CO_2H$)—$R_{14}$ in which $R_{14}$ is hydrogen or a group having the formula —$CHR_{15}R_{16}$ in which $R_{15}$ and $R_{16}$, independently, are hydrogen or $C_1$-$C_4$alkyl optionally substituted by one or two substituents selected from hydroxy, thio, methylthio, amino, carboxy, sulfo, phenyl, 4-hydroxyphenyl, 3,5-diiodo-4-hydroxyphenyl, β-indolyl, β-imidazolyl and NH=C($NH_2$)NH—.

4. A process according to claim 1 in which $R_{10}$ is an aminoacid residue derived from glycine, alanine, sarcosine, serine, cysteine, phenylalanine, tyrosine (4-hydroxyphenylalanine), diiodotyrosine, tryptophan (β-indolylalanine), histidine ((β-imidazolylalanine), α-aminobutyric acid, methionine, valine (α-aminoisovaleric acid), norvaline, leucine (α-aminoisocaproic acid), isoleucine (α-amino-β-methylvaleric acid), norleucine (α-amino-n-caproic acid), arginine, ornithine (α,δ-diaminovaleric acid), lysine (α,ε-diaminocaproic acid), aspartic acid (aminosuccinic acid), glutamic acid (α-aminoglutaric acid), threonine, hydroxyglutamic acid or taurine, or a mixture or optical isomer thereof.

5. A process according to claim 1 in which $R_{10}$ is an aminoacid residue derived from iminodiacetic acid.

6. A process according to claim 1 in which $R_{10}$ is an aminoacid residue derived from taurine, sarcosine, glutamic acid or iminodiacetic acid.

7. A process according to claim 1 in which $R_{10}$ is chloro, amino, phenyl, methylphenyl, dimethylphenyl, morpholino or an aminoacid residue from which a hydrogen atom on the amino group has been removed.

8. A process according to claim 1 in which $R_9$ is phenyl, methylphenyl, dimethylphenyl or a group of formula:

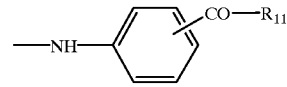

in which $R_{11}$ is defined in claim 1; and
$R_{10}$ is phenyl, methylphenyl, dimethylphenyl,

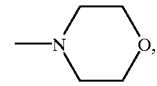

—$NH_2$, Cl, —$N(CH_2CH_2OH)_2$, —$N[CH_2CH(OH)CH_3]_2$ or an aminoacid residue from which a hydrogen atom on the amino group has been removed.

9. A process according to claim 8 in which $R_{11}$ is $C_1$-$C_4$-alkyl.

10. A process according to claim 8 in which $R_{11}$ is methyl or ethyl.

11. A process according to claim 1 in which the compound of formula (3) has the formula:

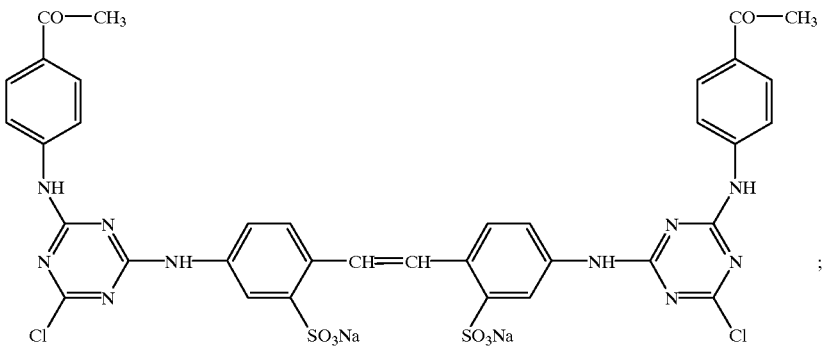

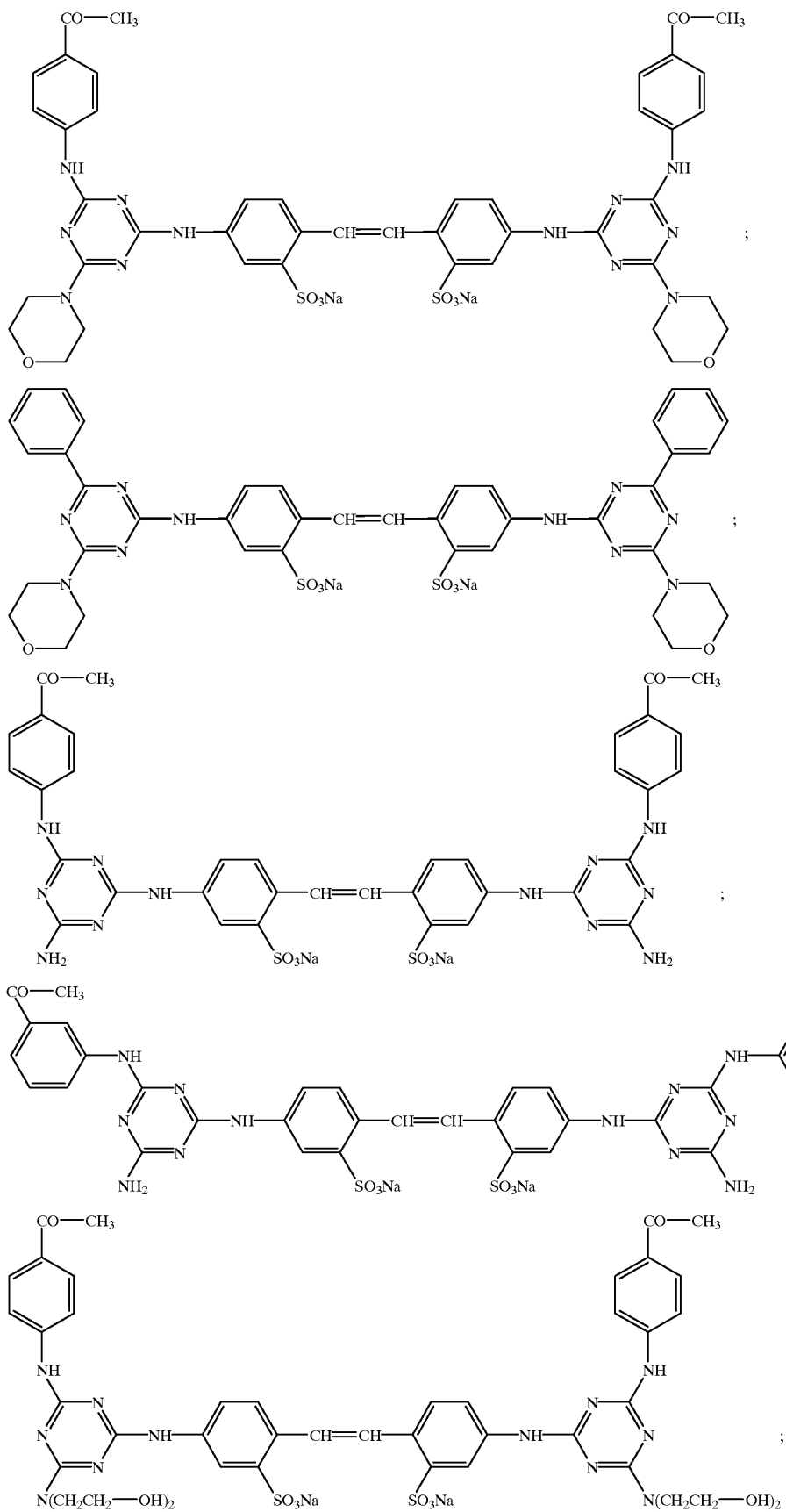

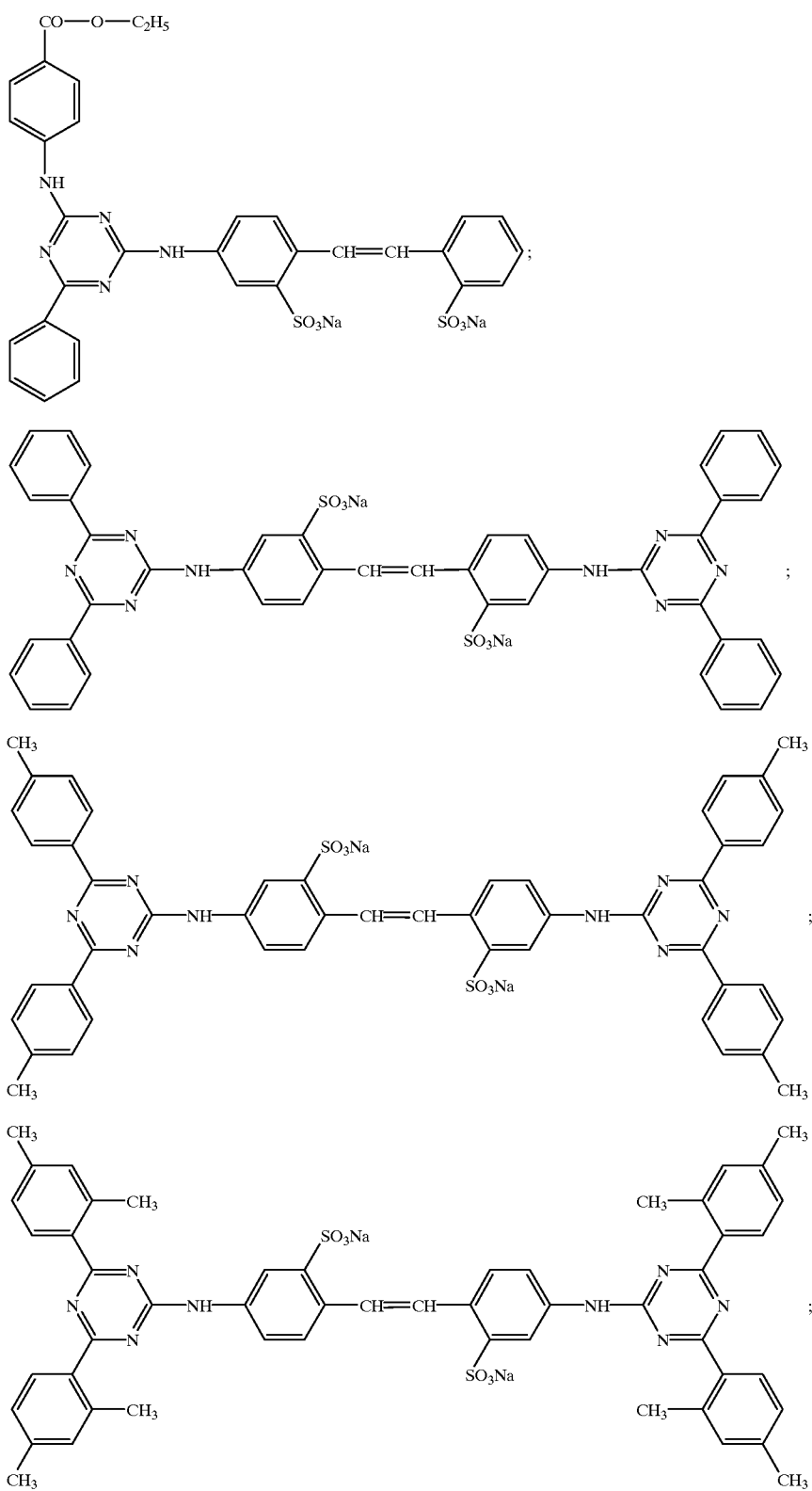

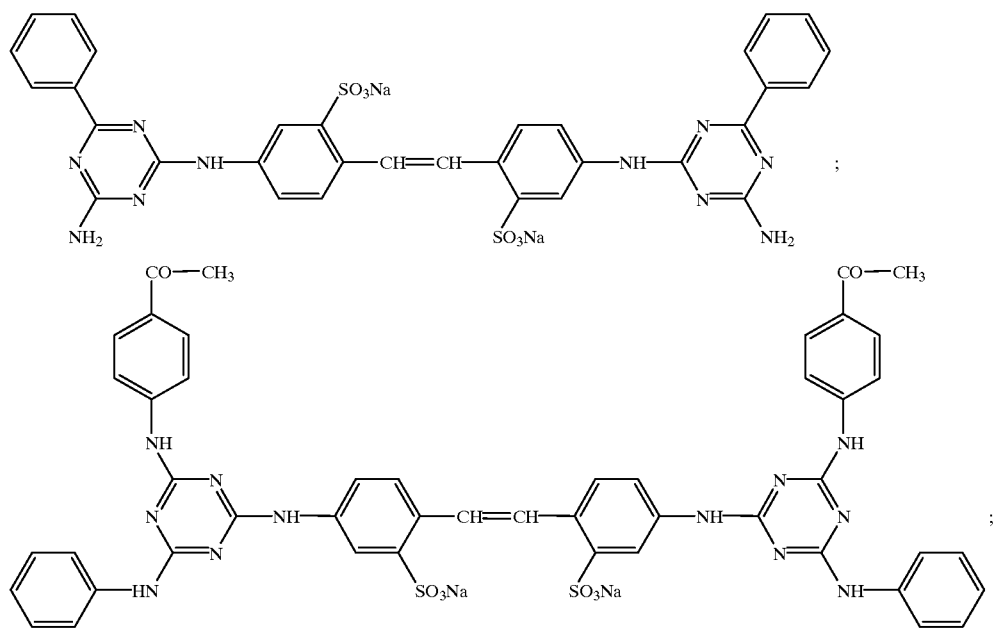
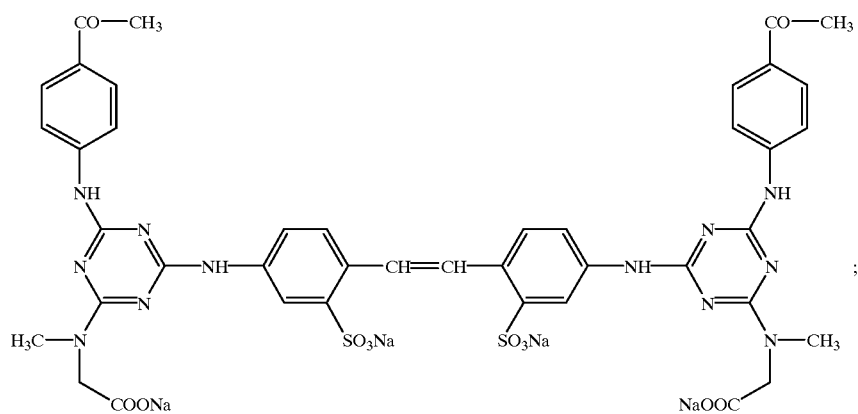
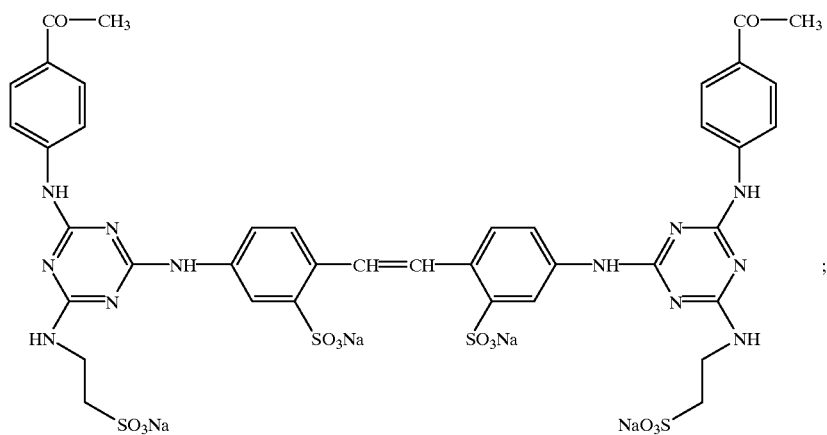

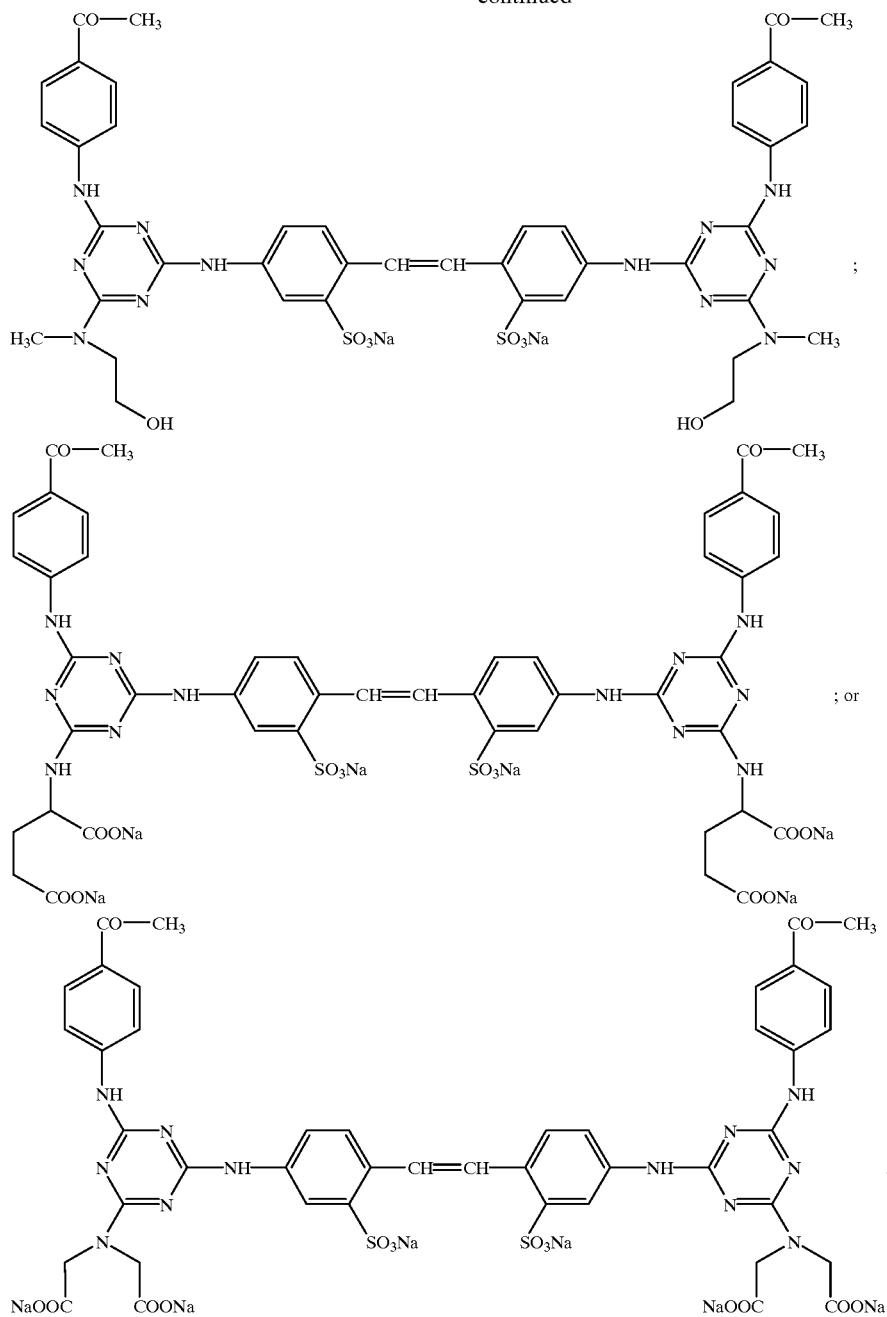
12. A process according to claim 1 in which the triazine-based ultra-violet absorption agent used as a quencher compound is used in an amount ranging from 0.5 to 50 times the amount of fluorescent whitening agent present in the substrate to be treated.
13. A substrate when treated according to a process claimed in claim 1.
* * * * *